United States Patent [19]

Andres et al.

[11] Patent Number: 5,260,460
[45] Date of Patent: Nov. 9, 1993

[54] PROCESS FOR THE PREPARATION OF FLUORINE-SUBSTITUTED AMINOBENZODIOXOLES AND -BENZODIOXANES AND NEW INTERMEDIATES

[75] Inventors: Peter Andres, Leichlingen; Albrecht Marhold, Leverkusen, both of Fed. Rep. of Germany

[73] Assignee: Bayer Aktiengesellschaft, Leverkusen, Fed. Rep. of Germany

[21] Appl. No.: 952,019

[22] Filed: Sep. 28, 1992

[30] Foreign Application Priority Data

Oct. 7, 1991 [DE] Fed. Rep. of Germany ....... 4133156

[51] Int. Cl.⁵ .................. C07D 319/20; C07D 317/62
[52] U.S. Cl. .................................. 549/362; 549/434; 549/439
[58] Field of Search ....................... 549/362, 434, 439

[56] References Cited

U.S. PATENT DOCUMENTS

| | | | |
|---|---|---|---|
| 4,250,187 | 2/1981 | Mues et al. | 549/434 |
| 4,722,935 | 2/1988 | Ehrenfreund | 514/465 |
| 4,886,816 | 12/1989 | Franckowiak et al. | 514/253 |

FOREIGN PATENT DOCUMENTS 2062888 10/1979 United Kingdom .

*Primary Examiner*—Nicky Chan
*Attorney, Agent, or Firm*—Sprung Horn Kramer & Woods

[57] ABSTRACT

According to the invention, a new process for the preparation of fluorine-substituted aminobenzodioxoles and -benzodioxanes of the formula (I)

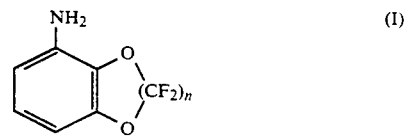

in which n represents an integer 1 or 2, has been found, in which fluorine-substituted nitrohalogeno-benzodioxoles and -benzodioxanes, which are likewise new, are hydrogenated. The novel intermediates are obtained from fluorine-substituted benzodioxoles and benzodioxanes by halogenation and subsequent nitration. The amino compounds are important starting materials for highly active biocides.

5 Claims, No Drawings

PROCESS FOR THE PREPARATION OF FLUORINE-SUBSTITUTED AMINOBENZODIOXOLES AND -BENZODIOXANES AND NEW INTERMEDIATES

The present invention relates to a new process for the preparation of fluorine-substituted aminobenzodioxoles and -benzodioxanes, which are used as useful starting compounds for the synthesis of highly active compounds for the control, for example, of pests, and additionally to new intermediates.

It is known that fluorine-substituted aminobenzodioxoles are obtainable when 4-carboxy-1,3-benzodioxole (cf. W. H. Perkin and V. M. Trikojus, J. Chem. Soc. 1926, 2925) is reacted with phosphorus pentachloride to give 2,2-dichloro-4-carbonyl chloride-1,3-benzodioxole, this is reacted with antimony trifluoride to give the corresponding trifluoro compound, from which the 4-carboxamide is prepared using ammonia and is reacted in a fourth and last step by Hofmann degradation, i.e. by reaction with bromine and alkali metal hydroxide to give the desired 2,2-difluoro-4-amino-1,3-benzodioxole (cf. EP-198,797).

The disadvantages of this known process are the four-step reaction. Additional disadvantages are the expensive reagents such as phosphorus pentachloride and antimony trifluoride, which additionally give problems with disposal, i.e. the waste and by-products thereof. In addition, the starting material to be employed — 4-carboxy-1,3-benzodioxole- is likewise obtainable via a multi-step synthesis. Overall, it can be stressed that access to the desired fluorine-substituted amino compounds via the amide is very costly and is not suitable for carrying out on a large scale.

It has now been found that the fluorine-substituted amino-benzodioxoles and -benzodioxanes of the general formula (I)

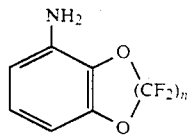

in which n represents an integer 1 or 2, are obtained when fluorine-substituted benzodioxoles or benzodioxanes of the formula (II)

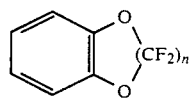

in which n has the abovementioned meaning, are halogenated in a first step in the presence of halogenation catalysts, if appropriate in the presence of solvents or diluents, and the halogen-substituted benzodioxoles and benzodioxanes thus obtainable of the formula (III)

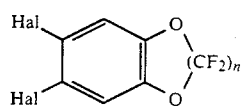

in which n has the abovementioned meaning and Hal represents halogen, preferably chlorine or bromine, are nitrated in a second step and the nitro compounds thus obtainable of the formula (IV)

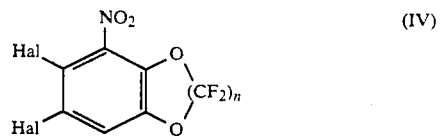

in which Hal and n have the meanings indicated, are catalytically hydrogenated in a solvent or diluent to give the compounds of the formula (I).

It is to be indicated as particularly surprising that according to the reaction according to the invention the desired products are obtained in high purity and good yields. Above all, it is surprising that the last step, the catalytic hydrogenation, both reduces the nitro group and removes the halogen atoms in the fused benzo ring without side reactions being observed.

Compared with the previously known process, the process according to the invention has a number of advantages:

In the first place, one reaction step is saved. In the second place, the starting material used, 2,2-difluoro-1,3-benzodioxole, can also be acquired in industrial quantities commercially. Furthermore, in the halogenation elemental halogen is employed, which yields only by-products escaping in gaseous form and thus does not pollute the waste water. While the phosphorus pentachloride to be employed in the known process forms phosphorus oxychloride as a reaction product, which necessitates special expenditure for separation. In addition, the use of expensive antimony trifluoride is avoided, whose by-products pollute the waste water and which is itself recoverable with difficulty. The palladium/carbon catalyst to be employed according to the invention in the third step can generally be disposed of by filtering off and is recoverable.

If, for example, 2,2-difluoro-1,3-benzodioxole, elemental chlorine in the presence of iron, then as the nitrating agent a nitric/sulphuric acid mixture (nitrating acid) and in the last step hydrogen and as the catalyst palladium-carbon are used, the course of the reaction of the process according to the invention can be represented by the following reaction scheme:

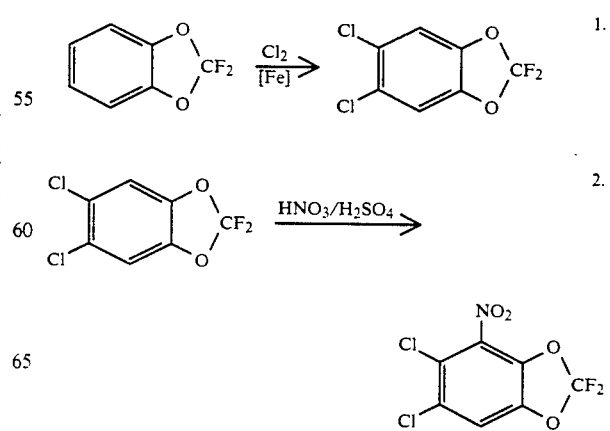

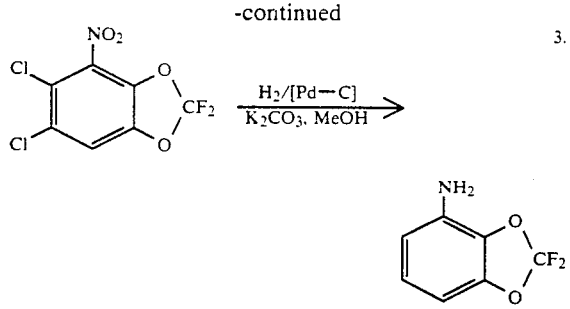

The fluorine-substituted benzodioxoles or benzodioxanes of the formula (II) required as starting substances for carrying out the process according to the invention are known and at least the dioxole can be acquired commercially, but all starting compounds can be prepared by analogous processes (DE 3,315,147=C.A. Vol. 102; 78862b and DE 3,642,256). The elemental halogen, the customary halogenation catalysts as well as the nitrating acid are common chemicals.

The halogen-substituted benzodioxoles or benzodioxanes of the formula (III) are new, but the halogenation is a well-known method (cf. DE 2,819,788). They are also a subject of the invention.

The intermediates of the formula (IV) additionally occurring are also new and likewise a subject of the invention. These new compounds are obtained from the compounds of formula III by nitration. Compare also the preparation examples.

The halogenating agents, employed in step 1, of compounds of the formula (II) to those of formula (III) are elemental halogens, preferably elemental chlorine or bromine.

The catalysts employed as halogenation catalysts in step 1 are customary Lewis acids, preferably iron and iron(III) chloride, iron(III) bromide and aluminium(III) chloride.

The 1st step is preferably carried out without solvent. Generally, however, solvents are suitable, for example chlorinated hydrocarbons, such as chloroform, dichloromethan and carbon tetrachloride.

The temperatures can be varied within a relatively wide range. In general, the reaction is carried out at temperatures between −80° C. and 160° C., preferably at temperatures between −30° C. and 80° C., particularly preferably at temperatures between −10° C. and 50° C.

The ratio of halogen to starting material of the formula (II) employed is preferably 2:1.

Step 2, the nitration step, is carried out with nitrating acid.

In general, step 2 is carried out without solvent.

The reaction temperatures can be varied within a relatively wide range. In general, the reaction is carried out at temperatures between −50° C. and 160° C., preferably at temperatures between −20° C. and 80° C., particularly at temperatures between −10° C. and 40° C.

The nitrating acid is employed relative to the starting material in general in a ratio of 2:1 to 10:1, preferably 4:1.

Step 3, the catalytic hydrogenation, is in general carried out in a solvent, for example in alcohols, such as methanol, or ethers, such as tetrahydrofuran.

Base additions used are preferably alkali metal carbonates, such as potassium carbonate, or tertiary amines, such as triethylamine, the ratio of base to starting material in general being 2:1.

The reaction temperatures in step 3 can be varied within a relatively wide range. The reaction is in general carried out at temperatures between 20° C. and 180° C., preferably at temperatures between 30° C. and 140° C., particularly preferably at temperatures between 30° C. and 100° C.

The hydrogen pressure is in general in the range between 1 and 200 bar, preferably in the range between 50 and 150 bar, particularly preferably in the range between 70 and 120 bar.

The fluorine-substituted amino-benzodioxoles and -benzodioxanes obtainable with the aid of the process according to the invention can be employed as starting compounds for highly active biocides, for example for the control of pests, preferably plant-damaging fungi, bacteria, insects and acarids. An example here is 2,2-difluoro-4-(2,4-dinitro-6-trifluoroanilino)-1,3-benzodioxole (cf. EP 198,797).

For example, the active substance mentioned as a microbicide is active against the phytopathogenic fungi belonging to the following classes: Fungi imperfecti (for example Botrytis, Helminthosporium, Fusarium, Septoria, Cercospora and Alternaria); Basidiomycetes (for example the genera Hemileia, Rhizocotonia, Puccinia); as well as against the Oomycetes belonging to the Phycomycetes class (for example Plasmopara viticola); in particular against the Ascomycetes class (for example Venturia, Podosphaera, Erysiphe, Monilinia, Uncinula). In addition to this, the compound has a systemic action. It can also be employed as a dressing agent for the treatment of seeds (fruits, tubers, grain) and plant seedlings for protection from fungal infections as well as against phytopathogenic fungi occurring in the soil.

As an insecticide, the compound can also be employed for controlling insects of the order: Lepidoptera, Coleoptera, Homoptera, Heteroptera, Diptera, Thysanoptera, Orthoptera, Blattaria, Anoplura, Siphonaptera, Mallophaga, Thysanura, Isoptera, Psocoptera and Hymenoptera.

The compound is furthermore suitable for the control of representatives of the order Acarina, for example the families Loxididae, Argasidae, Tetranychidae and Dermanyssidae. The compound can be successfully employed for controlling phytopathogenic mites, for example of the family Tetranychidae and Phytoptipalpidae (spider mites), Tarsonemidae (tarsonemids) and Ericphydiae (gall mites).

Besides their action against mosquitos and flies, such as, for example, *Aedes aegypti* and *Musca domestica*, the compound can also be employed for controlling plant-damaging feeding insects in ornamental and productive plantings, in particular in cotton crops (for example against *Spodoptera littoralis* and *Heliothis virescens*), and also in cereals, fruit and vegetable crops (for example against *Laspeyresia pomonella, Leptinotarsa decemlineata* and *Epilachna varivestis*). The compound is also distinquished by a good action against larval development stages and nymphs, in particular of feeding harmful insects.

The compound can also be used for controlling ectoparasitic insects and acarids on domestic animals and livestock, for example by animal, stable and pasture treatment.

Preparation Examples

1st step—Halogenation:

1a) 5,6-Dichloro-2,2-difluoro-benzo(1.3)dioxole

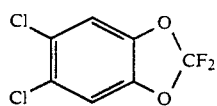

158 g (1 mol) of 2,2-difluorobenzo[1.3]dioxole are mixed with 1.5 g of iron powder and chlorinated with elemental chlorine with ice-cooling until the dichloro product is formed (gas chromatography checking about 8h). By distillation, 219 g (96% of theory) of 5,6-dichloro-2,2-difluoro-benzo (1.3)dioxole are obtained having boiling point$_{18}$: 74° to 78° C.

1b) 5,6-Dibromo-2,2-difluoro-benzo(1.3)dioxole

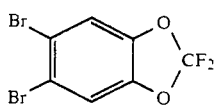

31.6 g (0.2 mol) of 2,2-difluorobenzo[1.3]dioxole are mixed with 0.5 g of iron powder. 64 g (0.4 mol) of bromine are then added dropwise with ice-cooling at an internal temperature of 25° C. with good stirring in the course of 2 h. After subsequently stirring at 30° C. for one hour, the mixture is added to water and extracted with methylene chloride, and the extract is dried over sodium sulphate and distilled in vacuo. 36 g (57% of theory) of 5,6-dibromo-2,2-difluoro-benzo (1.3)dioxole are obtained having a boiling point$_{18}$: 108° to 115° C.

2nd step-Nitration:

(2a) 5,6-dichloro-4-nitro-2,2-difluoro-benzo(1.3)dioxole

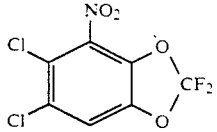

A precooled mixture of 140 ml of 100% strength nitric acid and 200 ml of 100% strength sulphuric acid is added dropwise at 5° to 10° C. (internal temperature) with good stirring to 219 g (0.96 mol) of 5,6-dichloro-2,2-difluorobenzo[1.3]dioxole. The reaction mixture is then subsequently stirred at room temperature for 6 h. It is added to ice-water and extracted with ether, and the extract is dried and concentrated. 233 g (89% of theory) of 5,6-dichloro-4-nitro-2,2-difluoro-benzo(1.3)dioxole having a melting point of 29°–30° C. are obtained.

2b) 6,7-Dibromo-5-nitro-2,2,3,3-tetrafluoro-benzo(1.4)-dioxane

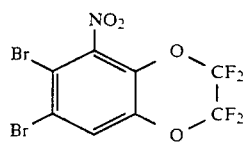

A precooled mixture of 19 ml of nitric acid and 26 ml of concentrated sulphuric acid is slowly added dropwise at 5° C. to 73 g (0.2 mol) of 6,7-dibromo-2,2,3,3-tetrafluoro-benzo (1.4)dioxane. The mixture is subsequently stirred at 5° C. for 4 hours, poured onto ice and extracted thoroughly with ether, the extract is washed with water and sodium hydrogen carbonate solution (until neutral), and dried over magnesium sulphate, and the ether is removed. 72 g (88% of theory) of 6,7-dibromo-5-nitro-2,2,3,3-tetrafluoro-benzo(1.4)dioxane having the melting point 91° to 92° C. are isolated.

3. Reduction of the NO$_2$ group and selective dehalogenation 3a) 4-Amino-2,2-difluoro-benzo(1.3)dioxole

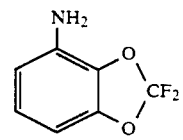

68 g (250 mmol) of 5,6-dichloro-4-nitro-2,2-difluoro-benzo(1.3)dioxole, 69 g (500 mmol) of potassium carbonate and 5 g of palladium-carbon. (10% strength) are stirred at 50° C. and a hydrogen pressure of 90 bar in 500 ml of methanol in an autoclave for 20 hours. The reaction mixture is filtered, the filtrate is mixed with 500 ml of water and extracted thoroughly with ether, the extract is dried over sodium sulphate and the ether is removed in a rotary evaporator. By distillation, 35 g (81% of theory) of 4-amino-2,2-difluoro-benzo(1.3)dioxole are obtained having a boiling point of 84° to 86° C./16 mm and a refractive index of n$^{21}_D$: 1.4995.

3b) 5-Amino-2,2,3,3-tetrafluoro-benzo(1.4)dioxane

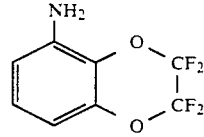

62 g (150 mmol) of 6,7-dibromo-5-nitro-2,2,3,3-tetrafluoro-benzo(1.4)dioxane, 41 g (300 mmol) of potassium carbonate and 5 g of palladium-carbon (10% strength) are stirred at 50° C. and a hydrogen pressure of 90 bar in 500 ml of methanol in an autoclave for 20 hours. The reaction mixture is filtered, the filtrate is mixed with 500 ml of water and extracted thoroughly with ether, and the extract is dried over sodium sulphate and concentrated. Vacuum distillation yields 26 g (78% of theory) of 5-amino-2,2,3,3-tetrafluoro-benzo(1.4)dioxane having a boiling point of 99° to 101° C./16 mm.

We claim:

1. Process for the preparation of fluorine-substituted amino-benzodioxoles and -benzodioxanes of the general formula (I)

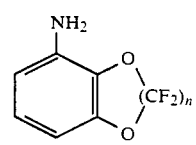

(I)

in which n represents an integer 1 or 2, by reaction of fluorine-substituted benzodioxoles or benzodioxanes of the formula (II)

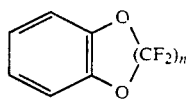

in which n has the abovementioned meaning, in a first step in the presence of halogenation catalysts, optionally in the presence of solvents or diluents, with halogen and the halogen-substituted benzodioxoles and benzodioxanes thus obtainable of the formula (III)

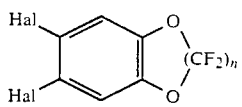

in which n has the abovementioned meaning and Hal represents halogen, in a second step with nitrating agents and the nitro compounds thus obtainable of the formula (IV)

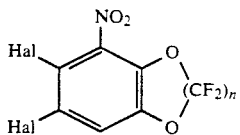

in which Hal and n have the meanings indicated, catalytically hydrogenate in a solvent or diluent to give the compounds of the formula (I), characterised in that the halogenation step 1 is carried out with elemental halogen in the presence of halogenation catalysts and optionally solvents, the nitration reaction of step 2 is carried out with nitrating acid without solvent and the hydrogenation of step 3 is carried with hydrogen in the presence of paladium catalysts in a solvent and optionally in the presence of a base.

2. Process according to claim 1, characterised in that the reaction is carried out in the first step in the temperature range between −80° C. and 160° C., in the second step in the temperature range between −50° C. and 160° C. and in the third step in the temperature range between 20° C. and 180° C.

3. Process according to claim 1, characterised in that the reaction is carried out in the first step in the temperature range between −30° C. and 80° C., in the second step in the temperature range between −20° C. and 80° C. and in the third step in the temperature range between 30° C. and 140° C.

4. Process according to claim 1, characterised in that iron or iron compounds are used in step 1 as halogenation catalysts.

5. Process according to claim 1, characterised in that the hydrogen pressure during the catalytic hydrogenation is in the range from 1 to 200 bar.

* * * * *